United States Patent
Leisner et al.

(10) Patent No.: US 6,966,901 B2
(45) Date of Patent: Nov. 22, 2005

(54) OSTOMY CARRIER DEVICE WITH FLEXIBLE FLANGE

(75) Inventors: Henrik Leisner, Gentofte (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 156 days.

(21) Appl. No.: 10/257,966

(22) PCT Filed: May 8, 2001

(86) PCT No.: PCT/DK01/00318

§ 371 (c)(1), (2), (4) Date: Oct. 25, 2002

(87) PCT Pub. No.: WO01/85074

PCT Pub. Date: Nov. 15, 2001

(65) Prior Publication Data

US 2003/0093042 A1    May 15, 2003

(30) Foreign Application Priority Data

May 8, 2000    (DK) ............................. 2000 00756

(51) Int. Cl.⁷ ................................................ A61F 5/44
(52) U.S. Cl. ..................................................... 604/337
(58) Field of Search ............................. 604/332–345, 604/355

(56) References Cited

U.S. PATENT DOCUMENTS

| | | | |
|---|---|---|---|
| 4,419,100 A | 12/1983 | Alexander | 604/339 |
| 4,828,553 A | 5/1989 | Nielsen | 604/339 |
| 5,015,244 A | 5/1991 | Cross | |
| 5,346,482 A | 9/1994 | Metz et al. | 604/338 |
| 5,496,296 A * | 3/1996 | Holmberg | 604/336 |
| 5,501,677 A * | 3/1996 | Jensen | 604/338 |

FOREIGN PATENT DOCUMENTS

| | | |
|---|---|---|
| EP | 0 276 042 | 7/1988 |
| EP | 0 476 847 A1 | 8/1991 |
| EP | 0 476 847 | 3/1992 |
| EP | 0 629 388 | 12/1994 |
| EP | 0 686 381 | 12/1995 |
| GB | 2 181 652 | 4/1987 |
| WO | 94/15562 | 7/1994 |
| WO | 96/38106 | 12/1996 |
| WO | WO 96/38106 | 12/1996 |
| WO | 98/17212 | 4/1998 |
| WO | WO 98/17212 | 4/1998 |
| WO | 98/34573 | 8/1998 |

* cited by examiner

Primary Examiner—Larry I. Schwartz
Assistant Examiner—Linh Truong
(74) Attorney, Agent, or Firm—Jacobson Holman PLLC

(57) ABSTRACT

A carrier device including a flexible adhesive base plate with an opening for securing the carrier device to a user's skin around a stoma, and a substantially circumferential flange made of a flexible material and adapted for removable and adhesive connection with a coupling element of an ostomy collecting bag. The outer portion of the flange is free to move relative to the base plate and is more flexible than the inner portion of the flange. As a result, the outer portion can absorb movements between the carrier device and the collecting bag, thus protecting against peeling of the bond between the flange members as well as providing a cushioning effect against forces acting on the periphery of the flanges, while the less flexible inner portion can withstand deformations originating from the adhesive base plate.

24 Claims, 4 Drawing Sheets

OSTOMY CARRIER DEVICE WITH FLEXIBLE FLANGE

This is a nationalization of PCT/DK01/00318, filed May 8, 2001 and published in English.

BACKGROUND OF THE INVENTION

1. Field of the Invention

The present invention relates to an ostomy carrier device adapted for use in a collecting system for use by patients having a stoma. More specifically the present invention relates to an ostomy carrier device comprising a flexible adhesive base plate with an opening for securing the carrier device to a patient's, or user's, skin around a stoma, as well as a circumferential mounting flange made of a flexible material and being adapted for removable and adhesive connection with a coupling element of an ostomy collecting bag, the carrier device and the collecting bag making up a collecting system.

2. Description of the Related Art

In collecting systems in general, the base plate of the carrier device must be able to remain on the user over a long period of time, for example up to 8–10 days. During this whole period of time, the carrier device must be capable of withstanding deformation due to the user's movements, washing, exposure to bag replacements, etc. Conventionally, the base plate of such a carrier device is designed as a thin adhesive wafer or pad, to which is attached a coupling means for coupling the carrier device to a collecting bag. In the collecting systems which until now have been dominant on the market, the coupling has been provided by first and second relatively rigid coupling rings on the base plate and collecting bag, respectively, the coupling rings being detachably connectable to each other. When such a rigid ring system is attached to the base, movements and deformations to the base plate will not influence the locking engagement between the coupling rings, this resulting in a long-lasting connection between the collecting bag and the base plate.

However, the above conventional system has a number of drawbacks. For example, the rigid coupling rings may be uncomfortable for the user during use as they prevent the base plate from following the contours of the body when the user moves, and it does not provide the desired shock absorbing effect between the collecting bag and the user, which, of course, reduces comfort. Further, such a coupling ring system is relatively bulky and thus difficult to hide behind many types of garment, this presenting a cosmetic and aesthetic problem to many users and thus a reduced acceptance.

In the past proposals have been suggested for novel and improved coupling systems overcoming the above problems. One such system relies on a coupling comprising a circumferential flange firmly attached to the base plate and made of a flexible material being adapted for removable and adhesive connection with a coupling element of a ostomy collecting bag. Another similar system comprises a circumferential flange attached to the base plate corresponding to the inner edge portion of the flange, the outer portion of the flange being free to move relative to the base plate.

The carrier devices of the above-described systems have proven very comfortable to wear; however, due to a number of problems such systems have until now not been successful.

One problem with these systems arises when the flexible flange is forced to follow the movements of the base plate, this resulting in a tendency for the collecting bag to detach from the flange. It is believed that this is due to stretching of the flange material resulting in reduced adhering properties of the flange surface, especially when the material of one of the flanges is non-adhesive, the adhesive being on either the coupling element of the collecting bag or the base plate flange. Eventually a leak will be formed which, indeed, is unacceptable to the user.

One attempt to overcome these problems is described in EP 0 276 042 disclosing a base plate with a relatively rigid flange attached, the adhesive connection taught between bag and carrier device being provided by a number of layers of adhesive applied to the flange of the base plate and activated one after the other, which limits the number of times the bag can be changed to the number of layers of adhesive. Use of such rigid flange member may serve to protect the bond between the flange member and the collecting bag; however, it reintroduces the rigidity of the above described coupling ring system. Furthermore, a new problem is introduced as the rigid flange member allows the coupling element on the ostomy bag to peel off as the collecting bag moves relative to the carrier device during normal use of the system.

A different approach to negotiate the above problems is described in WO 96/38106 in which a soft flexible ring of a foam material is mounted on the base plate, this allowing the base plate flange and the flexible connecting flange of a collecting bag mounted thereon to move relative to the base plate. This approach reduces the tendency of the adhesive bond between the carrier device and the collecting bag to break up, however, after removal of the used collecting bag, the deformations to the foam ring thereby introduced will leave an uneven or wrinkled surface for the next collecting bag to be mounted, thereby jeopardising the sealing action.

SUMMARY OF THE INVENTION

In the light of this, an object of the present invention is to provide an improved carrier device, which helps remedy one or more of the above described problems. More specifically, an object is to provide a carrier device, which ensures a safe and reliable bond between the carrier device and the attached collecting hag and yet provides a high degree of wearing comfort.

The present invention is based on the recognition that the different portions of the mounting flange serve different specialised functions. More specifically, it has been found by the present inventors that the innermost portion of the flange should be adapted to withstand movements as well as deformation of the flexible adhesive base plate in order to prevent pealing of the bond to start from the inner edge, whereas the outermost portion of the flange should be adapted to withstand the external forces applied to the bond due to, primarily, movements of the collection bag which arise during use thereof. Indeed, in combination the inner and outer portions of the flange should ensure against axially directed pulling forces applied on the bag.

A first choice to protect a flexible inner portion of a coupling flange against excessive deformation originating from the adhesive base plate would be to make the latter thicker and stiffer. Such a solution can be easily implemented and is found to work well, the relatively stiff base plate protecting the mounting flange from "curling". However, the present inventors have found that this solution will only work for a relatively short period of time after which peeling will start from the inner edge of the bond. The reason for this has been found to be due to long-term (i.e. over days) plastic deformation, or "creeping", of the adhesive base plate material normally used for this purpose.

Thus, if it would be possible to base a solution on these recognitions, an ostomy collecting system would be provided that combines the best properties of the known systems: high resistance to leakage yet providing excellent comfort for the user.

According to the invention, the above is achieved by a carrier device comprising a flexible adhesive base plate with an opening for securing the carrier device to a user's skin around a stoma, and a substantially circumferential flange made of a flexible material and being adapted for removable and adhesive connection with a coupling element of a ostomy collecting bag, wherein the outer portion of the flange is free to move relative to the base plate and the outer portion of the flange is more flexible than the inner portion of the flange. This latter feature ensures that the outer peripheral portion of the flange can absorb movements between the carrier device and the collecting bag thus protecting against peeling of the bond between the flange members as well as providing a cushioning effect against forces acting on the periphery of the flanges, whereas the inner less flexible portion is adapted to withstand deformations originating from the adhesive pad. Preferably the flange is a relatively thin, substantially planar sheet or foil-like structure.

Although it is considered that the expression "more flexible" is clear to the skilled person within this technical field, i.e. properties with regard to flexibility which meet the stated objects of the invention, it could be defined that the average flexibility of the outer portion is at least 10%, preferably at least 20% higher than the average flexibility of the inner portion. Such an "average flexibility" would be relevant as, for example, the outer portion may comprise segments, e.g. ring-formed, which would locally be less flexible than the outer portion in general. It may very well be that for a given carrier device a difference of only 10% will solve the stated problem, whereas for another carrier device a difference of more than 100% will be necessary. Indeed, for a flange made of a single material, the above considerations would apply to the thickness of the different portions of the flange, i.e. the average thickness of the outer portion is correspondingly at least 5%, preferably at least 10% less than the average thickness of the inner portion.

In the context of the present invention the term "circumferential" implies only that a member provides a structure surrounding an opening; such a member may have circular inner and outer edges, however, it could have any combination of, for example, round, oval or angular shapes.

When it is stated that an outer portion of the flange is free to move with respect to the base plate, this means that only an inner edge or a part of the inner portion of the flange is attached to the base plate, while the remainder of the flange is free to move relative thereto.

When the carrier device defines a general plane of reference, it is clear to the skilled person that no strictly mathematical plane is defined but a plane represented by the carrier device itself, such a device having a generally planar configuration. When the body side member is attached to the user, the plane of reference will be substantially parallel with the user's skin.

According to a preferred embodiment of the invention, a hinge is formed between the outer and inner portions of the flange, such a hinge providing an "un-coupling" of the inner and outer portions allowing the two portions to serve their respective purposes even better. More specifically, a hinge will be able to distribute the forces acting on the inner portion of the flange, and thus the stoma, when the outer portion is subject to external forces during use, this providing increased carrying comfort. Further, the hinge will be able to reduce the amount of deformation which is transferred from the inner to the outer portion of the flange, this reducing the risk that peeling starting from the inner edge of the flange will spread to the outer portion and ultimately to the outer edge of the flange, which then would amount to a leak being formed. The hinge may be formed with a thickness, which is less than the thickness of the inner and outer portions of the flange to which it connects, or it may be formed by a material having a desired high flexibility.

According to a further preferred embodiment, the flange has a coupling surface facing away from the base plate and defining an attachment area, an outer circumferential portion of the flange corresponding to at least 50% of the area being free to move with respect to the other members of the carrier device. This construction allows an adhesive coupling member of a collecting bag to be fastened primarily or entirely on this free portion, which ensures adequate protection against peeling action as well as against forces applied to the collecting bag that are transmitted directly to the base plate.

BRIEF DESCRIPTION OF THE DRAWINGS

The invention will now be described in further detail below with reference to the schematic drawing, in which.

DETAILED DESCRIPTION OF THE PREFERRED EMBODIMENTS

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
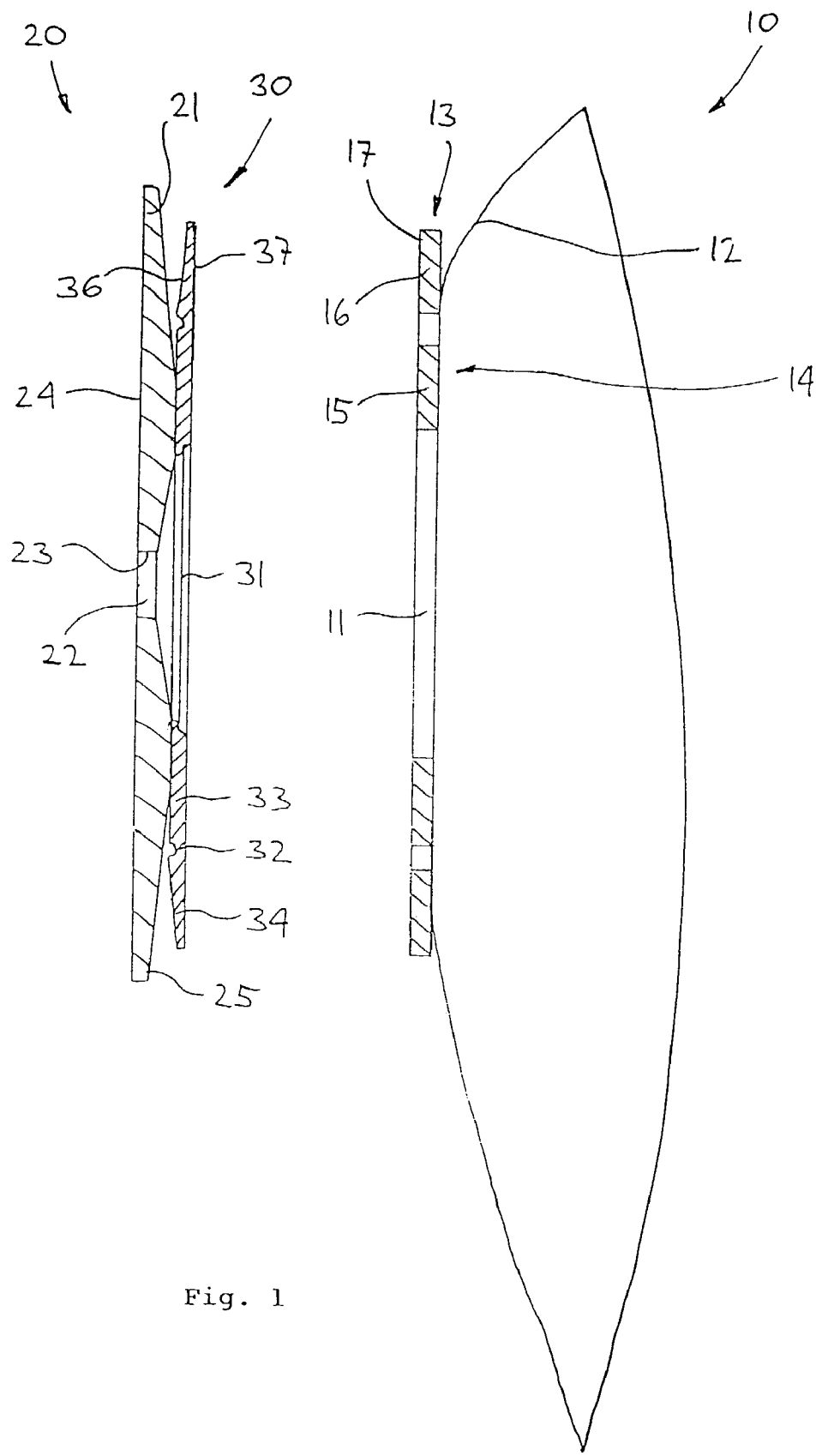
FIG. 1 is a sectional view of a carrier device according to the invention and a collecting bag to be mounted on the carrier device.

The ostomy collecting system shown in FIG. 1 comprises a. collecting bag 10 for collection of faeces and a carrier device 20 with a circumferential flange 30 for fastening the bag 10 around an intestinal orifice in the form of a so-called stoma in a user's abdominal wall (not shown), and for this purpose it has an inlet opening 11 in a bag wall 12. The bag 10 may either be closed at the bottom as shown or configured with a drainage device for discharging its contents. The inlet opening 11 is surrounded by connecting means for connecting the bag 10 with the flange 30 of the carrier device 20.

In the shown embodiment, the connecting means on the bag 10 is in the form of a second flange or bag flange 13 which is fastened to the bag wall 12 by means of a substantially circumferential attachment means defining an attachment zone 14 in such a manner that a rim portion of the bag flange 13 protrudes outwardly beyond the attachment zone. The bag flange 13 may be fastened to the bag wall 12 through any suitable means, for example directly by heat or UV welding or by means of an adhesive. In the shown embodiment the bag flange comprises two concentric rings 15, 16 connected to each other only at a number of narrow bridges (not to be seen in the figure). The two rings are adapted for mounting on an inner respectively an outer portion of the flange 30 and allow the bag flange to flex easily together with the hinge formed between the inner and outer portions of the flange 30. On the side facing away from the bag, the flange 13 is coated across substantially its entire surface with a thin layer 17 of adhesive, which may, for example, be a hydrogel adhesive, an acrylate adhesive or an adhesive of the hot-melt type. The layer 17 of adhesive is applied thinly, partly to keep down the thickness, partly to maintain the flexibility and resilience of the bag flange 13. This application may be effected, for example, by coating, spraying or application in a suitable pattern. In the delivery state of the bag, the layer 17 of adhesive is typically protected by a release liner (not shown) covering the layer.

The carrier device comprises a circumferential base plate 21 with an opening 22 and an inner free edge 23, and is designed to be adhered to the user's skin by means of a skin-friendly adhesive applied on the lower surface 24 of the base plate intended for attachment to the skin of the user. Preferably the peripheral portion of base plate is formed with a reduced thickness in order to better comply with movements and folding of the skin surface of the patient. The base plate 21 carries a flange or base plate flange 30 on its opposite upper surface 25, in which is formed an opening 31 providing communication between the opening 11 in the bag and the opening 22 in the base plate when the bag is mounted on the carrier device. The flange has a first surface 36 facing towards the base plate, a second opposite surface 37 facing away from the base plate, the second surface of the flange being adapted for removable and adhesive connection with the ostomy collecting bag. In the shown embodiment a hinge 32 is formed between an inner portion 33 and an outer portion 34 of the flange. In the shown embodiment, the different portions of the flange 30 is manufactured from the same material, and the hinge is formed with a thickness, which is less than the thickness of the inner and outer portions of the flange to which it connects. In order to provide a higher flexibility of the outer portion as compared with the inner portion, the outer portion is formed with a reduced thickness as compared with the inner portion. The flange is attached to the base plate corresponding to the reduced thickness innermost edge portion of the flange, the reduced thickness providing improved heat transfer during the heat bonding process. Indeed, the flange may be attached by any suitable means just as the bond formed between the base plate and the flange may correspond to a smaller or larger area of the inner portion of the flange.

As it appears, the flange 30 is mounted at a distance from the opening 22, allowing the base plate portion surrounding the opening to be cut to provide an opening of a desired size in order to closely fit around the stoma of the user. In the delivery state of the carrier device, the adhesive lower surface 24 of the base plate is typically protected by a release liner (not shown) covering the layer. In the shown embodiment, the flange 30 is non-adhesive; however, the carrier device may also be provided with an adhesive base plate flange 30 adapted to match a non-adhesive bag flange 13, in which case a release liner would be provided on the base plate flange. Recently, adhesives have come on the market that are applied to both surfaces, but are before attachment non-sticking, thereby alleviating the necessity for a release liner.

With reference to FIGS. 2a–2e different embodiments for a flange member to be used in combination with a carrier device according to the invention will now be described.

In general, FIGS. 2a–2e illustrate partial cross sections corresponding to the FIG. 1 embodiment, but showing only one half of the carrier device. Further, the base plate is shown only in FIG. 2a. The base plate 200 and the flange 100 as well as the different structures thereof are only shown to illustrate their relative placement; neither their relative size nor their form represents specifically preferred embodiments, but are merely illustrative. The bonds between the base plate and the flange are shown only schematically in order to illustrate the position thereof, however, they may be formed in any suitable way such as by adhesive or welding. It is evident that for all embodiments the different bonds represent full, circumferential attachment sections as otherwise leakage between the different structures may occur.

Figure 2A:
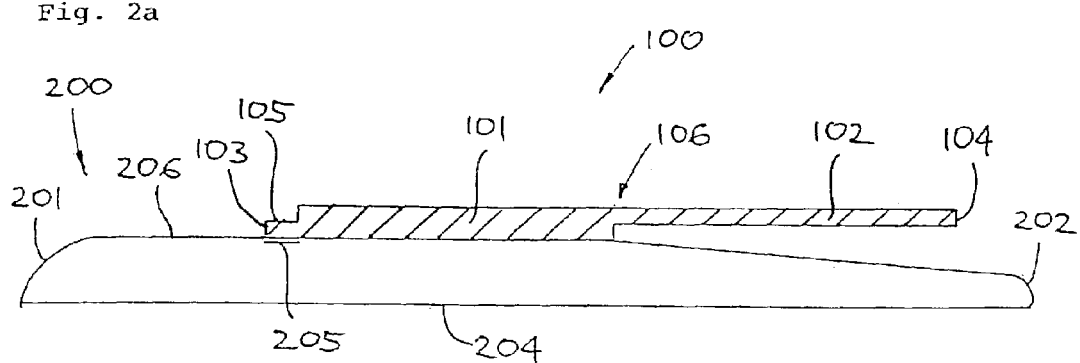
FIGS. 2a–2f show different embodiments of a flange to be used as part of a carrier device according to the invention.

FIG. 2a illustrates an embodiment comprising a flange 100 and a base plate 200. The flange 100 comprises an inner circumferential portion 100 with an inner edge 103 and an outer circumferential portion 102 with an outer free edge 104. In accordance with the object of the invention, the outer portion is formed with a reduced thickness to provide a higher degree of flexibility as compared with the inner portion. The transition area 106 between the two portions will establish a "virtual" hinge function between the two portions. The innermost part 105 of the inner portion in the vicinity of the inner edge is formed with a reduced thickness, this allowing a good transfer of heat in a heat welding process thus assuring a narrow bond 205 with reduced risk of heat damage to the flange and/or base plate. The base plate 200 comprises an inner edge 201, an outer edge 202, a lower adhesive surface 204 and an upper surface 206 on which the flange is attached at 205 corresponding to the inner edge portion of the flange, the flange being attached at a distance from the inner edge of the base plate. Although the flange is shown attached to the base plate only at the inner edge portion of the flange, the inner portion of the flange may be attached to the base plate to a greater extent just as it may be attached in patterns different from circumferential rings. The outer portion of the base plate is formed with a progressively reduced thickness towards the outer edge.

Figure 2B:
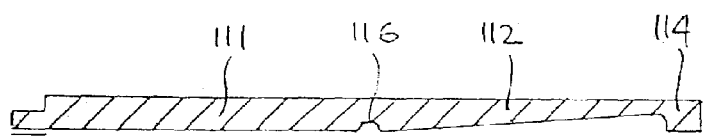

In the FIG. 2b embodiment a circumferential hinge 116 is formed between the inner and outer portions 111, 112 of the flange, the hinge having a thickness, which is less than the thickness of the portions of the flange to which it connects, preferably less than 75% of the thickness of the inner portion of the flange. For a preferred embodiment it has been found that the location of the hinge should be determined by the expression $1,1 \times R1 < R2 < (2 \times R3 + R1)/3$, wherein the inner edge of the flange has a radius $R1$, the outer edge of the flange has a radius $R3$, the radial location of a the hinge being determined by a radius $R2$. The circumferential hinge need not be a continuous structure but could be formed of circumferentially arranged hinge portions, preferably arcuate portions, arranged between stiffer bridge members connecting the inner and outer portions of the flange. Also, the hinge (as well as the other structures of the carrier device) need not to be circular but could, for example, be oval in order to be placed with a given preferred orientation when the carrier device is mounted around a stoma. As illustrated, the outer portion 112 is formed with a progressively reduced thickness towards the outer edge, the outer edge portion itself having an increased thickness in order to improve handling during mounting and bag exchange procedures.

Figure 2C:
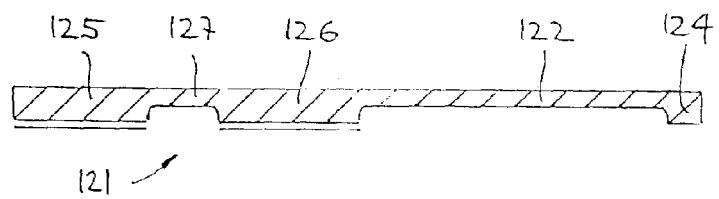

In the FIG. 2c embodiment the inner portion 121 of the flange is formed as two ring-segments 125, 126 connected by a circumferential bridge portion 127 which will allow the two rings to bend relative to each other. In contrast to the above-described embodiments, the flange is attached to the base plate corresponding to a major part of the inner portion, essentially corresponding to the lower surface of the two ring-segments. Although the increased rigidity of the inner portion will provide improved protection against leaking starting from the inner edge, the shown bridge portion will allow a "break up" of a spreading leak, just as the added flexibility provided by the bridge also improves carrying comfort. As above, the outer edge portion 124 is formed with an increased thickness. The FIG. 2c embodiment also illustrates that the general expression that the outer portion of the flange is more flexible (or of reduced thickness) is not to be interpreted literally as meaning that this is the case for every individual component of the respective inner and outer portions of the flange. In fact, the peripheral edge portion 124 will have a higher rigidity (i.e. having a higher modulus of elasticity) as compared with the bridge, however, this does not change the fact that for the skilled person it is clear that the outer portion 122 has an increased flexibility as compared with the inner portion 121, this as defined in the accompanying claims.

Figure 2D:

FIG. 2d shows an embodiment in which the flange 130 is of uniform thickness, the different flexibilities of the inner portion 131 and outer portion 132 of the flange being based solely on the choice of different materials for the two portions. Evidently, the inner portion 131 is formed from a material more rigid than the material used for the outer portion 132.

Figure 2E:
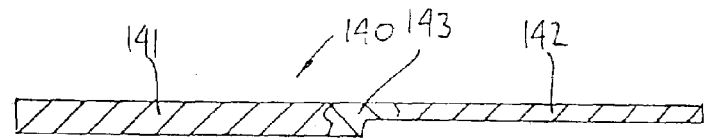

FIG. 2e shows an embodiment in which the flange 140 has a configuration similar to that of FIG. 2a, however, instead of a reduced-thickness hinge as in FIG. 2b, a hinge is formed by using a more flexible material for the circumferential transition area 143 between the inner 141 and outer 142 portions of the flange 140. As explained with respect to FIG. 2a, the hinge may be a continuos or a non-continuous structure.

Figure 2F:
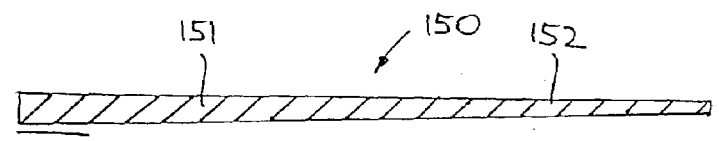

Although fully within the scope of the present invention, FIG. 2f shows an embodiment in which it is not possible to structurally define an inner and an outer portion, respectively, for the flange 150. However, in accordance with the invention, the inner less flexible portion may be defined as having a width (i.e. in the radial direction of the flange defined between the inner and outer edge) within 15–85%, preferably 25–75%, and more preferably 35–65% of the overall width of the flange. Preferably a portion of the inner portion of the flange is free to move relative to the base plate (as illustrated in FIGS. 2a–2f), such that the width of the moveable portion of the inner portion of the flange is within 15–85%, preferably 25–75%, and more preferably 35–65% of the general width of the flange.

In the above, the description has been based on the "traditional" annular form of a carrier device, however, a carrier device according to the invention, as well as its different components, may have any other desired configuration, e.g. oval or angular, just as the attachment between the flange and the base plate may be of any desirable form, e.g. wave-formed or in any discrete or non-uniform pattern. In order to properly distinguish preferred embodiments of the invention for such formed carrier devices, the moveable portion of the inner portion of the flange may be defined based on the areas for the different portions of the flange. Thus, in a preferred embodiment the area of the moveable portion of the inner portion of the flange is within 10–90%; preferably 25–75%, and more preferably 35–65% of the total area of the flange.

Figure 3:
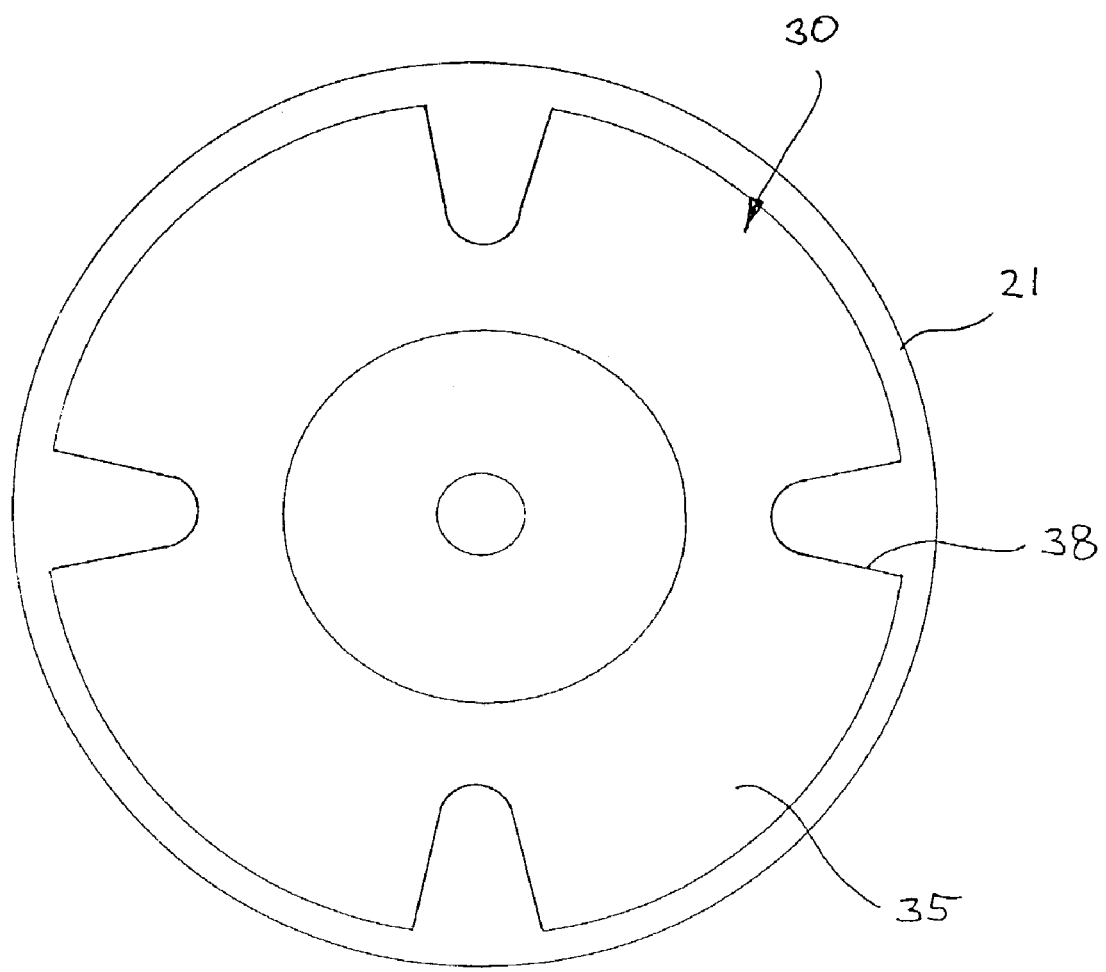
FIG. 3 shows an embodiment in which the flange consists of a number of leafs.

As indicated above, the flange and base plate have been described as circumferential structures, however, in order to secure a proper sealing action around the stoma, it suffices if only one single "complete" circumferential structure is formed around the stoma. Thus, in the context of the present application, the term "circumferential" also comprises structures arranged around an opening but having radial partitions. FIG. 3 illustrates such an embodiment in which the flange 30 consists of a number of "leafs" 35 arranged radially outwards from the central opening and between cut-out portions. Indeed, such an arrangement necessitates that the adhesive connection between the carrier device and the collecting bag incorporates the circumferential support member. Further, to avoid adhesive sticking to the base plate, the adhesive portions of the bag flange should be arranged corresponding to the inner support member and the individual leafs.

Figure 4:
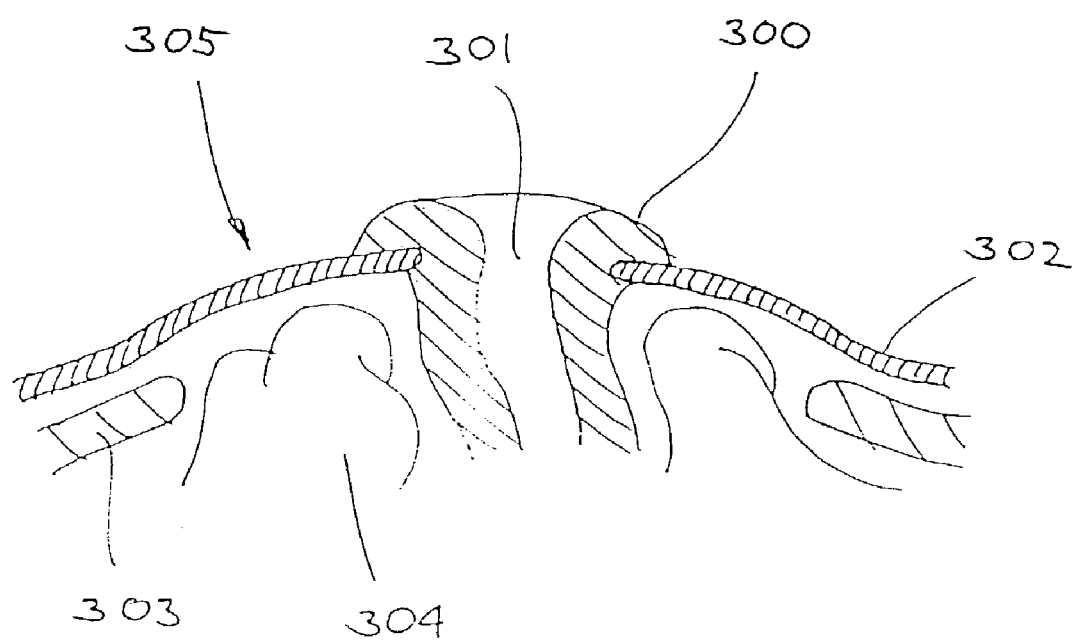
FIG. 4 shows an open end of an intestine of a patient, which has been attached to the abdominal wall to form a stoma.

FIG. 4 illustrates how an open end of the intestine 300 of a patient has been attached to the abdominal wall 302 to form a stoma 301. Typically the intestine is arranged to protrude somewhat from the skin surface. When the abdominal wall is cut to provide a stoma during surgical procedures, very often an opening will develop as the deeper layers 303 of the abdominal wall are not closed around the stoma, this allowing the viscera 304 to bulge somewhat through this deep opening thereby creating a small or large bulge 305, a so-called hernia, around the stoma. When the patient moves, the viscera in the hernial opening may move in and out with the result that the bulge falls and rises. When a ostomy carrier device is mounted around the stoma, especially the "falling" will result in deformation of the inner portions of the carrier device leading to a wave-like curling and subsequent lift-off of the adhesive bond between the flanges of carrier device and the bag flange, however, in accordance with the invention, the more rigid inner portion of the carrier flange will reduce the tendency that such deformations will result in the onset of peeling and subsequent leakage.

While in the foregoing different embodiments of the invention have been disclosed in detail for purpose of illustration, it will be understood by those skilled in the art that many of these details may be varied without departing from the scope of the present invention as defined in the accompanying claims.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An ostomy carrier device comprising:
    a flexible adhesive base plate for securing the carrier device to a user's skin around a stoma, the base plate having an opening for receiving the stoma;
    a circumferential flange made of a flexible material connected to the base plate, the circumferential flange having a first surface facing towards the base plate, a second opposite surface facing away from the base plate, an inner portion with an inner edge, an outer portion with an outer edge, and a substantially circumferential hinge formed between and being more flexible than the outer and inner portions of said flange, said flange being attached to the base plate corresponding to an innermost edge portion of the flange, the second surface of the flange being adapted for removable and adhesive connection with an ostomy collecting bag;
    said carrier device defining a general plane of reference, a thickness thereof being defined in a direction perpendicular thereto;

said outer portion of the flange being free to move relative to the base plate; and the outer portion of the flange being more flexible than the inner portion of the flange.

2. The ostomy carrier device as defined in claim 1, wherein at least a portion of the inner portion of the flange is free to move relative to the base plate.

3. The ostomy carrier device as defined in claim 1, wherein the flange has an overall width in the radial direction defined between the inner edge and the outer edge, a width of the inner portion of the flange constituting between 15–85 of said overall width of the flange.

4. The ostomy carrier device as defined in claim 2, wherein a width of the moveable portion of the inner portion of the flange constitutes between 15–85 of an overall width of the flange as defined in the radial direction between the inner and outer edges.

5. The ostomy carrier device as defined in claim 2, wherein an area of the moveable portion of the inner portion of the flange constitutes between 10–90 of a total area of the flange.

6. The ostomy carrier device as defined in claim 1, wherein the flange is connected to the base plate in the vicinity of the inner edge of the flange.

7. The ostomy carrier device as defined in claim 1, wherein the inner and outer portions of the flange are made substantially of the same type of material.

8. The ostomy carrier device as defined in claim 5, wherein the inner portion of the flange has a first average thickness and the outer portion of the flange has a second average thickness less than the first thickness.

9. The ostomy carrier device as defined in claim 1, wherein the inner portion of the flange is formed from a material having a higher modulus of elasticity than the material from which the outer portion of the flange is formed.

10. The ostomy carrier device as defined in claim 1, wherein the hinge has a thickness which is less than the thickness of the inner and outer portions of the flange to which it connects.

11. The ostomy carrier device as defined in claim 1, wherein the hinge is formed from a material more flexible than a material of the flange portions to which it connects.

12. The ostomy carrier device as defined in claim 1, wherein the inner edge of the flange has a radius R1, the outer edge of the flange has a radius R3, the radial location of the hinge being determined by a radius R2, wherein $1,1 \times R1 < R2 < (2 \times R3 + R1)/3$.

13. The ostomy carrier device as defined in claim 1, wherein the first surface is substantially planar.

14. The ostomy carrier device as defined in claim 1, in combination with a collecting bag.

15. The ostomy carrier device and collecting bag as defined in claim 14, the collecting bag comprises a bag flange with an adhesive portion such that an adhesive sealing connection can be formed between the ostomy collecting bag and the flange of the carrier device, the adhesive of the collecting bag being arranged such that it can be attached entirely on that portion of the flange which is free to move relative to the base plate.

16. The ostomy carrier device as defined in claim 1, wherein the flange has an overall width in the radial direction defined between the inner and outer edges, a width of said inner portion of the flange constituting between 25–75% of said overall flange width.

17. The ostomy carrier device as defined in claim 1, wherein the flange has an overall width in the radial direction defined between the inner and outer edges, a width of said inner portion of the flange constituting between 35–65% of said overall flange width.

18. The ostomy carrier device as defined in claim 2, wherein the flange has an overall width in the radial direction defined between the inner and outer edges, a width of said moveable portion of the inner portion of the flange constituting between 25–75% of said overall flange width.

19. The ostomy carrier device as defined in claim 2, wherein the flange has an overall width in the radial direction defined between the inner and outer edges, a width of said moveable portion of the inner portion of the flange constituting between 35–65% of said overall flange width.

20. The ostomy carrier device as defined in claim 2, wherein an area of the moveable portion of the inner portion of the flange constitutes between 25–75% of a total area of the flange.

21. The ostomy carrier device as defined in claim 2, wherein an area of the moveable portion of the inner portion of the flange constitutes between 35–65% of a total area of the flange.

22. An ostomy carrier device comprising:
a flexible adhesive base plate for securing the carrier device to a user's skin around a stoma, the base plate having an opening for receiving the stoma;
a circumferential flange made of a flexible material and having a surface adapted for removable and adhesive connection with an ostomy collecting bag, an inner portion of said flange being connected to the base plate and an outer portion of said flange being free to move relative to said base plate, said outer flange portion being more flexible than said inner flange portion, and a substantially circumferential hinge being formed between and being more flexible than the outer and inner portions of said flange.

23. An ostomy carrier device comprising:
a flexible adhesive base plate for securing the carrier device to a user's skin around a stoma, the base plate having an opening for receiving the stoma;
a circumferential flange made of a flexible material and having a surface adapted for removable and adhesive connection with an ostomy collecting bag, an inner portion of said flange being connected to the base plate and an outer portion of said flange being free to move relative to said base plate, said outer flange portion being more flexible than said inner flange portion, and a transition area between the inner and outer portions of said flange having a thickness less than a thickness of said inner and outer portions.

24. An ostomy carrier device comprising:
a flexible adhesive base plate for securing the carrier device to a user's skin around a stoma, the base plate having an opening for receiving the stoma;
a circumferential flange made of a flexible material and having a surface adapted for removable and adhesive connection with an ostomy collecting bag, an inner portion of said flange being connected to the base plate and an outer portion of said flange being free to move relative to said base plate, said outer flange portion being more flexible than said inner flange portion, and a transition area between the inner and outer portions of said flange being formed from a material that is more flexible than a material of said inner and outer portions.

* * * * *